(12) United States Patent
Dessain et al.

(10) Patent No.: US 8,557,575 B2
(45) Date of Patent: *Oct. 15, 2013

(54) FUSION PARTNER CELL LINE FOR PREPARATION OF HYBRID CELLS EXPRESSING HUMAN ANTIBODIES

(75) Inventors: Scott K. Dessain, Wynnewood, PA (US); Sharad P. Adekar, Secane, PA (US)

(73) Assignee: Thomas Jefferson University, Philadelphia, PA (US)

( * ) Notice: Subject to any disclaimer, the term of this patent is extended or adjusted under 35 U.S.C. 154(b) by 371 days.

This patent is subject to a terminal disclaimer.

(21) Appl. No.: 12/864,896

(22) PCT Filed: Jan. 28, 2009

(86) PCT No.: PCT/US2009/000561
§ 371 (c)(1),
(2), (4) Date: Sep. 17, 2010

(87) PCT Pub. No.: WO2009/131605
PCT Pub. Date: Oct. 29, 2009

(65) Prior Publication Data
US 2011/0008344 A1 Jan. 13, 2011

Related U.S. Application Data

(60) Provisional application No. 61/062,639, filed on Jan. 28, 2008.

(51) Int. Cl.
*C12N 5/00* (2006.01)
(52) U.S. Cl.
USPC .......................................................... 435/346
(58) Field of Classification Search
None
See application file for complete search history.

(56) References Cited

U.S. PATENT DOCUMENTS

| 2002/0150580 A1 | 10/2002 | Newman et al. ........... 424/154.1 |
| 2003/0219861 A1 | 11/2003 | Rother et al. ................ 435/69.1 |
| 2006/0235207 A1 | 10/2006 | Tsuchiya et al. ........... 530/388.8 |

FOREIGN PATENT DOCUMENTS

| WO | WO 2004/023973 A2 | 3/2004 |
| WO | WO 2009/105150 A2 | 8/2009 |

OTHER PUBLICATIONS

Adekar et al (Human Antibodies, 2008, v.17 pp. 33-38).*
Adekar et al (Hybridoma, 2008, v.27:1, pp. 11-17).*
ATCC Product Description: ATCC CRL-1823 (K6H6/B5) (www.atc.org.common/catalog/numSearch/numResults.cfm?collection=ce&atccNum . . .) (accessed May 9, 2006).
HyperCLDB K6H6/B5 (ECACC 89101606) mouse/human, heterohybridoma), www.biotech.ist.unique.it/cldb/c12994.html) (accessed May 9, 2006).
PubMed Abstract 3084658: Carroll et al, "Mouse x human heterohybridomas as fusion partners with human B cell tumors", *J. Immunol Methods*, May 1, 1986: 89(1): 61-72.
Dessain, et al., "High efficiency creation of human monoclonal antibody-producing hybridomas", *Journal of Immunological Methods* 291 (2004) 109-122.
Borrebaeck, et al., "Human monoclonal antibodies produced by primary in vitro immunization of peripheral blood lymphocytes", *Proc. Natl. Acad. Sci. USA*, vol. 85, pp. 3995-3999, Jun. 1988.
PubMed Abstract 7492449: Delvig, et al., "Comparison of three human-murine heteromyeloma cell lines for formation of human hybridomas after electrofusion with human peripheral blood lymphocytes from meningococcal cases and carriers", *Hum Antibodies Hybridomas*, 1995: 6(2): 42-6.
Final Oral & Poster Programs, Conference Program for: 14th International Conference on Human Antibodies and Hybridomas, Nov. 12-14, 2008, pp. 39-43.

* cited by examiner

*Primary Examiner* — Brad Duffy
(74) *Attorney, Agent, or Firm* — Drinker Biddle & Reath LLP

(57) ABSTRACT

This invention relates to a novel fusion partner cell line that ectopically expresses IL-6 and TERT termed B5-6T, and to methods for making the B5-6T fusion partner cell line. The B5-6T fusion partner cell line can be fused with B-lymphocytes to generate hybridomas that secrete human monoclonal antibodies.

7 Claims, 5 Drawing Sheets

SEQ ID NO: 1
caggtgcagctggtggagtctgggggagggttagtacagccagggcggtccctgagactctcctgtacagcctct
ggattcacctttggtgattctgccatgagctgggtccgccaggctccagggaaggggctggagtgggtaggtttcat
tagaggtaaaccttatggagggaaaccagaatacgccgcgtctgtgaaaggcagattcaccatttcaagagacg
attccaagagcatcgcctatctgcaaatgaacagcctgaaaaccgaggacacagccgtgtattactgtactgca
gggatgactacggtgactatttatgactactggggccagggaaccctggtcaccgtctcctcagcaagcaccaag SEQ ID NO: 2
ggattcacctttggtgattctgccatgagctgggtccgccaggctccagggaaggggctggagtgggtaggtttcat
tagaggtaaaccttatggagggaaaccagaatacgccgcgtctgtgaaaggcagattcaccatttcaagagacg
attccaagagcatcgcctatctgcaaatgaacagcctgaaaaccgaggacacagccgtgtattactgtactgca
gggatgactacggtgactatttatgactactgg SEQ ID NO: 3
EVQLVESGGGLVQPGRSLRLSCTASGFTFGDSAMSWVRQAPGKGLEWVGFIR
KPYGGKPEYAASVKGRFTISRDDSKSIAYLQMNSLKTEDTAVYYCTAGMTTVTIY
DYWGQGTLVTVSSASTK SEQ ID NO: 4
GFTFGDSAMSWVRQAPGKGLEWVGFIRKPYGGKPEYAASVKGRFTISRDDSKS
IAYLQMNSLKTEDTAVYYCTAGMTTVTIYDYW

Figure 4A

SEQ ID NO: 5
cagccactctcagtgtcagtggccctgggacagacggccggaattacctgtgagggaaacaacattggaag
taaaaatgtgcattggtaccagcagaagccaggccaggcccctgtgctggtcatctatagggatagcaatcg
gccctctgggatccctgagcgattctctggcttcaactcggggaatacggccaccctgaccatcagcagagtc
caagccggggatgaggctgactattactgtcaggtgtgggacagcagcactggggtgttcggcggagggac
cgagctgaccgtcctaggtcagcccaaggctgccccctcggtcactctgttcccgccctcctctgaggagcttc
aagccaacaaggccacactggtgtgtctcataagtgacttctacccgggagccgtgacagtggcctggaagg
cagatagcagccccgtcaaggcgggagtggagaccaccacaccctccaaacaaagcaacaacaagtac
gcggccagcagctatctgagcctgacgcctgagcagtggaagtcccacagaagctacagctgccagg SEQ ID NO: 6
aacattggaagtaaaaatgtgcattggtaccagcagaagccaggccaggcccctgtgctggtcatctatagg
gatagcaatcggccctctgggatccctgagcgattctctggcttcaactcggggaatacggccaccctgaccat
cagcagagtccaagccggggatgaggctgactattactgtcaggtgtgggacagcagcactggggtgttc SEQ ID NO: 7
QPLSVSVALGQTAGITCEGNNIGSKNVHWYQQKPGQAPVLVIYRDSNRPSGI
PERFSGFNSGNTATLTISRVQAGDEADYYCQVWDSSTGVFGGGTELTVLGQ
PKAAPSVTLFPPSSEELQANKATLVCLISDFYPGAVTVAWKADSSPVKAGVET
TTPSKQSNNKYAASSYLSLTPEQWKSHRSYSCQ SEQ ID NO: 8
NIGSKNVHWYQQKPGQAPVLVIYRDSNRPSGIPERFSGFNSGNTATLTISRVQ
AGDEADYYCQVWDSSTGVF

Figure 4B

FUSION PARTNER CELL LINE FOR PREPARATION OF HYBRID CELLS EXPRESSING HUMAN ANTIBODIES

REFERENCE TO GOVERNMENT GRANT

This invention was supported in part by grant number R01 AI065967 from the National Institutes of Health. The U.S. Government has certain rights in this invention.

FIELD OF THE INVENTION

The invention relates to a fusion partner cell line for use in making hybridomas that secrete human monoclonal antibodies. The invention also relates to a hybridoma so modified, and antibodies secreted from the hybridoma.

BACKGROUND OF THE INVENTION

Many problems associated with antisera were circumvented with the seminal discovery of mouse hybridomas capable of secreting specific monoclonal antibodies (MAbs) against predefined antigens by Kohler and Milstein (Kohler G. and Milstein C., 1975 Nature 256: 495). Since the report of Kohler and Milstein, the production of mouse monoclonal antibodies has become routine.

Monoclonal antibodies are produced by hybrid cells that result from a fusion between normal B-lymphocytes and myeloma cells. The myeloma cell lines used for fusion are B-lymphocyte tumor cell lines that grow well in vitro and can propagate indefinitely, in contrast to normal B-lymphocytes that cannot replicate or produce antibody in vitro for more than a few days. Cells derived from a fusion of the two types of cells combine the in vitro growth characteristics of the myeloma cell line with the production of an antibody derived from the B-lymphocyte.

Hybrid cells (hybridomas) are generally produced from mass fusions between murine splenocytes, which are highly enriched for B-lymphocytes, and myeloma "fusion partner cells" (B. Alberts et al., Molecular Biology of the Cell (Garland Publishing, Inc. 1994); E. Harlow et al., Antibodies. A Laboratory Manual (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are called monoclonal antibodies.

However, progress in making fully human monoclonal antibodies has been hampered by the absence of human myeloma suitable for use as fusion partners with the desirable attributes of mouse myeloma cells such as stability, and high antibody production. The use of Epstein-Barr virus (EBV) has proved to be quite efficient for human lymphocyte immortalization (Kozbor D, and Roder J., J. Immunology 1981; 127:1275; Casual O, Science 1986; 234:476), but has certain limitations such as low antibody secretion rate, poor clonogenicity of antibody-secreting lines and chromosomal instability necessitating frequent subcloning.

Many investigators have attempted to generate human monoclonal antibodies by generating hybridomas with human B-lymphocytes (N. Chiorazzi et al, J. Exp. Med. 156: 930 (1982); C. M. Croce et al., Nature 288:488 (1980); P. A. Edwards et al, Eur. J. Immunol. 12:641 (1982); R. Nowinski et al, Science 210:537 (1980); L. Olsson et al, Proc. Natl. Acad. Sci. USA 77:5429; J. W. Pickering et al, J. Immunol. 129:406 (1982)). Unfortunately, these hybrid cells exhibited poor growth in vitro, low levels of antibody expression, instability of antibody expression, and a poor ability to be cloned by limiting dilution.

Consequently, diverse and cumbersome approaches have been used to produce human monoclonal antibodies. These include "humanizing" mouse antibodies by creating hybrid murine/hybrid immunoglobulin genes and generating antibodies in transgenic mice that bear human immunoglobulin gene loci. However, these methods are only able to produce antibodies that have been generated in mice by the murine immune system. They do not allow the isolation, production, and use of the naturally-occurring antibodies, the immunological memory that the human immune system produces in response to infections and other antigen exposures. The ability to make monoclonal antibodies directly from human B-lymphocytes is therefore needed and would be of considerable value.

Recently, there has been progress in generating human monoclonal antibodies by generating hybridomas using the SP2/0 cell line as a fusion partner. The SP2/0 cell line is an immortal murine myeloma cell line (a malignant B-lineage cell) that expresses an endogenous murine telomerase gene. U.S. Patent Application Publication No. 20030224490 discloses the genetic modification of the SP2/0 cell line to ectopically express interleukin-6 (IL-6) and human telomerase catalytic subunit (hTERT).

However, there have been some shortcomings with the applicability and effectiveness of using the modified SP2/0 cell line as the fusion partner. It has been observed that the aforementioned modified SP2/0 cell line is unstable and losses the expression of hTERT after a period of culturing. This inability to at least maintain hTERT expression presents an obstacle for generating human monoclonal antibodies at a high frequency. In some instances, hybridomas derived from the modified SP2/0 cell line are unable to be adapted to culturing in serum-free medium. The inability for hybridomas to be cultured in serum-free medium complicates the purification process of the secreted antibodies. Thus, there is a need to develop better fusion partners for the generation of human antibodies.

Another fusion partner cell line that has been used for generating hybridomas that secrete human monoclonal antibodies is the K6H6-B5 heteromyeloma cell line (Carroll et al., 1986 J. Immunol. Methods 89: 61-72; CRL-1823, ATCC, Manassas, Va.). However, it has been shown that this fusion partner cell line produce hybridomas at a low frequency and only a small percentage of those clones are stable and are able to secrete antibodies through three rounds of cell culturing. See Watkins et al., (U.S. Pat. No. 6,787,638).

Since the original report describing the creation of hybridomas expressing murine monoclonal antibodies, adaptation of this method to human antibody cloning has been a desirable yet elusive goal. Thus, there is a great need for fusion partner cell lines that are stable, fuse well with human lymphocytes, and result in hybridomas that stably produce fully humanized antibodies at a high frequency. A desirable fusion partner cell line for making fully human monoclonal antibody-producing hybridomas should ideally meet the following requirements. It should: 1) produce no or negligible amounts of endogenous immunoglobulin (Ig) or individual immunoglobulin chains; 2) have a short doubling time; 3) grow in suspension culture; 4) be suitable for high efficiency fusion with B-lymphocytes of different histological origin; 5) be non-biased (non-selective in terms of Ig type) in fusion to B-lymphocytes producing different Ig isotypes; 6) yield stable Ig-producing hybrids capable of long-term stable production of specific Ig's; 7) and be easily adaptable to serum-free media and culturing in bioreactors for mass production of monoclonal antibodies. The present invention satisfies the need for such a desirable fusion partner cell line.

Botulism is a life-threatening, flaccid paralysis caused by a neurotoxin produced by the anaerobic bacterium *Clostridium botulinum*. Botulinum neurotoxin poisoning (botulism) arises in a number of contexts including, but not limited to food poisoning (food borne botulism), infected wounds (wound botulism), and "infant botulism" from ingestion of spores and production of toxin in the intestine of infants. Botulism is a paralytic disease that typically begins with cranial nerve involvement and progresses caudally to involve the extremities. In acute cases, botulism can prove fatal.

Botulinum neurotoxin (BoNT) is found in nature as seven antigenically distinguishable proteins (serotypes A, B, C1, D, E, F, and G). Botulinum neurotoxin acts at neuromuscular junctions. In addition BoNT has been designated as a category A select bioterrorism agent by the United States Government because of its extreme lethality and its availability from environmental sources (Arnon et al., 2001 JAMA 285: 1059-70; Greenfield and Bronze, 2003 Drug Discov. Today 8:881-8; Marks, 2004 Anesthesiol. Clin. North America 22:509-32). An inhaled lethal dose of BoNT for a 70 kg person is less than 1 microgram; 1 gram contains enough BoNT to kill one million people (Arnon et al., 2001 JAMA 285:1059-70). Thus, devastatingly lethal amounts of BoNT could easily be transported and distributed in secret. Because of the requirement for immediate and prolonged ICU support for exposure victims, a limited civilian exposure could easily overwhelm the intensive care unit capability of a typical American city (NIAID, 2002b).

The chief countermeasures for BoNT exposure have historically been the botulinum toxoid vaccine and therapeutic antibodies. The existing vaccine is an inactivated pentavalent toxoid that induces a potent neutralizing antibody response (Arnon et al., 2001 JAMA 285:1059-70; Gelzleichter et al. 1999 J. Appl. Toxicol. Suppl. 1:S35-8; Siegel, 1998 Immunol. Res. 17:239-51). However, it has not been recommended for use in the general population because the naturally occurring disease is rare and widespread vaccination would render vaccinees resistant to BoNT, which may be required for medical indications such as blepharospasm, dystonia and torticollis (Bell et al., 2000 Pharmacotherapy 20:1079-91). Use of the toxoid vaccine following BoNT exposure is of no value because it is slow to induce a neutralizing antibody response (Arnon et al., 2001 JAMA 285:1059-70).

The effectiveness of therapeutic antibody treatments for BoNT exposure is well established. BoNT-neutralizing immunoglobulin (BoNT-Ig) given prior to BoNT exposure can prevent or eliminate complications (Arnon et al., 2001 JAMA 285:1059-70; Gelzleichter et al. 1999 J. Appl. Toxicol. Suppl. 1:S35-8; Siegel, 1998 Immunol. Res. 17:239-51). BoNT-Ig given after exposure can prevent progression of symptoms, although it cannot reverse synaptic injury that has already occurred. However, the effectiveness of the presently available BoNT-neutralizing antibodies is limited. Thus, there is a need for further therapeutic antibodies for BoNT. The present invention satisfies this need.

SUMMARY OF THE INVENTION

The invention provides a fusion partner cell line deposited as ATCC accession number PTA-8869. The invention also provides a hybridoma deposited as ATCC accession number PTA-8871.

In one embodiment, the invention provides a monoclonal antibody produced from hybridoma 13A (ATCC accession no. PTA-8871). The antibody provided by said hybridoma may be referenced to herein as "13A". 13A may also be used to refer to said hybridoma.

The invention also provides a method of making a hybridoma. The method comprises fusing B-lymphocytes to the fusion partner cell line deposited as ATCC accession number PTA-8869, thereby producing a hybridoma. In one embodiment, B-lymphocytes are cultured in vitro for a period of time in the presence of pokeweed mitogen prior to fusing with the fusion partner cell line deposited as ATCC accession number PTA-8869. In another embodiment, the B-lymphocytes are isolated from a subject vaccinated with a botulinum vaccine.

The invention provides a method of producing a monoclonal antibody. The method comprises fusing B-lymphocytes with the fusion partner cell line deposited as ATCC accession number PTA-8869 to produce hybridomas, selecting a hybridoma that produces a monoclonal antibody, and culturing the hybridoma to produce the monoclonal antibody. In one embodiment, B-lymphocytes are cultured in vitro for a period of time in the presence of pokeweed mitogen prior to fusing with the fusion partner cell line deposited as ATCC accession number PTA-8869. In another embodiment, the B-lymphocytes are isolated from a subject vaccinated with a botulinum vaccine. Preferably, the hybridoma is cultured in serum free medium.

The invention provides a method of producing a monoclonal antibody comprising culturing the hybridoma deposited as ATCC accession number PTA-8871, and obtaining the antibody produced by the hybridoma. In one embodiment, the method includes culturing the hybridoma in serum-free medium.

The invention includes a monoclonal antibody produced by culturing the hybridoma deposited as ATCC accession number PTA-8871, and obtaining the antibody produced by the hybridoma. The invention also includes antigen-binding fragments of the antibody.

The invention includes an antibody that specifically binds to an epitope specifically bound by an antibody produced by the hybridoma deposited as ATCC accession number PTA-8871.

In another embodiment, the invention provides an isolated antibody comprising an antibody heavy chain variable domain having an amino acid sequence of SEQ ID NO: 4; and an antibody light chain variable domain having an amino acid sequence of SEQ ID NO: 8. The invention also provides for fragments of the antibody including, but not limited to a single chain Fv (scFv) fragment, a Fab fragment, a (Fab')$_2$ fragment, and a (scFv')$_2$ fragment.

In another embodiment, the antibody comprises an antibody heavy chain variable domain having an amino acid sequence of SEQ ID NO: 4; and an antibody light chain variable domain having an amino acid sequence of SEQ ID NO: 8.

The invention also provides a method of treating or preventing toxicity in an individual due to botulinum neurotoxin exposure. The invention also provides a method of neutralizing BoNT/A in a subject. The method comprises administering to the subject an effective amount of an antibody or antigen-binding fragment thereof that binds and neutralizes BoNT/A, wherein the antibody specifically binds to an epitope bound by an antibody produced by the hybridoma deposited as ATCC accession number PTA-8871.

The invention also provides an isolated nucleic acid molecule encoding at least one of the antibody heavy chain polypeptide comprising the amino acid sequence SEQ ID NO: 3 and the antibody light chain polypeptide comprising the amino acid sequence SEQ ID NO: 7.

In one embodiment, the isolated nucleic acid molecule comprises a first nucleic acid segment encoding the antibody heavy chain polypeptide comprising the amino acid sequence SEQ ID NO: 3 and a second nucleic acid segment encoding the antibody light chain polypeptide comprising the amino acid sequence SEQ ID NO: 7.

In another embodiment, the isolated nucleic acid molecule comprises a sequence selected from the group consisting of SEQ ID NO: 1, SEQ ID NO: 5, and any combination thereof.

The invention also provides an isolated nucleic acid molecule encoding at least one of the antibody heavy chain variable domain comprising the amino acid sequence SEQ ID NO: 4 and the antibody light chain variable domain comprising the amino acid sequence SEQ ID NO: 8.

In one embodiment, the isolated nucleic acid molecule comprises a first nucleic acid segment encoding the antibody heavy chain variable domain comprising the amino acid sequence SEQ ID NO: 2 and a second nucleic acid segment encoding the antibody light chain variable domain comprising the amino acid sequence SEQ ID NO: 6.

In another embodiment, the isolated nucleic acid molecule comprises a sequence selected from the group consisting of SEQ ID NO: 2, SEQ ID NO: 6, and any combination thereof.

Any antibody as described above can be used in medicine. For example, the invention encompasses the use of an antibody as described above for the preparation of a medicament for neutralizing the effects of botulinum toxin in a subject.

ABBREVIATIONS AND SHORT FORMS

The following abbreviations and short forms are used in this specification.

"BoNT/A" means botulinum neurotoxin serotype A.
"CDR" means complementarity determining region.
"ELISA" means enzyme-linked immunosorbent assay.
"FR" means framework.
"huMAb" means human monoclonal antibody.
"Ig" means immunoglobulin.
"Ig H" means immunoglobulin heavy chain.
"Ig L" means immunoglobulin light chain.
"MAb" means monoclonal antibody.
"PCR" means polymerase chain reaction.
"RT-PCR" means reverse transcription PCR.
"scFv" means single chain variable fragment.
"IL" means interleukin.
"hTERT" means human telomerase catalytic subunit.

DEFINITIONS

The definitions used in this application are for illustrative purposes and do not limit the scope of the invention.

The articles "a" and "an" are used herein to refer to one or to more than one (e.g., to at least one) of the grammatical object of the article. By way of example, "an element" means one element or more than one element.

An "antigen" is any agent, e.g., a protein (or immunogenic fragments), a peptide or peptide conjugate, immunogen, vaccine, or a polysaccharide, that elicits an immune response. For example, an immunogenic bolutinum toxin molecule can comprise full length botulinum toxin, or immuogenic fragments thereof. A boultinum vaccine can also be used to elicit an immune response in a animal.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The term "antibody" as used herein refers to an immunoglobulin molecule that contains an antigen binding site which specifically binds an antigen. Structurally, the antibody comprises four polypeptide chains, two heavy (H) chains and two light (L) chains inter-connected by disulfide bonds. The term also encompasses polyclonal and monoclonal antibodies, hybrid, and humanized antibodies.

As used herein, "antibody fragments" or "antigen-binding fragments" are fragments of an antibody, such as Fab, F(ab')$_2$, Fv fragments, and single chain variable fragments (scFv), which are capable of binding an epitopic determinant. Antibody fragments can refer to antigen-binding immunoglobulin peptides which are at least about 5 to about 15 amino acids or more in length, and which retain some biological activity or immunological activity of an immunoglobulin. Examples of binding fragments encompassed within the term "antigen-binding fragments" include but are not limited to (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544-546) which consists of a VH domain; (v) an isolated complimentarity determining region (CDR); and (vi) an F(ab')$_2$ fragment, a bivalent fragment comprising two Fab fragments linked by a disulfide bridge at the hinge region. Furthermore, although the two domains of the Fv fragment are generally coded for by separate genes, a synthetic linker can be made that enables them to be made as a single protein chain (known as single chain Fv (scFv); Bird et al. (1988) Science 242:423-426; and Huston et al. (1988) PNAS 85:5879-5883) by recombinant methods. Such single chain antibodies are also encompassed within the term "antigen-binding fragments". Preferred antibody fragments are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations.

As used herein, the term "monoclonal antibody" includes antibodies which display a single binding specificity and affinity for a particular epitope. These antibodies are mammalian-derived antibodies, including murine, human and humanized antibodies. The term "human monoclonal antibody" as used herein, refers to antibodies displaying a single binding specificity which have variable and constant regions derived from human germ-line immunoglobulin sequences.

"Biologically active," as used herein with respect to botulinum neurotoxin neutralizing antibodies, fragments, derivatives, homologs, and analogs means that the antibodies, fragments, derivatives, homologs or analogs have the ability to neutralize a botulinum neurotoxin, as described herein (e.g. BoNT/A).

As used herein, an "effective amount" or "therapeutically effective amount" of botulinum neurotoxin neutralizing antibodies, is an amount sufficient to neutralize (mitigate or eliminate) BoNT/A toxin (e.g., reduce or eliminate a symptom of BoNT/A poisoning (botulism)).

The term "expression," as used with respect to a botulinum neurotoxin neutralizing antibody mRNA, refers to transcription of a botulinum neurotoxin neutralizing heavy or light chain nucleic acid sequence, resulting in synthesis of botulinum neurotoxin neutralizing antibody mRNA. "Expression," as used with respect to a botulinum neurotoxin neutralizing antibody, refers to translation of a botulinum neurotoxin neutralizing antibody mRNA, resulting in synthesis of a botulinum neurotoxin neutralizing antibody.

As used herein, the term "fragment" or "segment" as applied to a nucleic acid, refers to a subsequence of a larger nucleic acid. A "fragment" or "segment" of a nucleic acid can be at least about 20 nucleotides in length; for example, at least about 50 nucleotides to about 100 nucleotides; preferably at least about 100 to about 500 nucleotides, more preferably at least about 500 to about 1000 nucleotides, even more preferably at least about 1000 nucleotides to about 1500 nucleotides; particularly, preferably at least about 1500 nucleotides to about 2500 nucleotides; most preferably at least about 2500 nucleotides.

As used herein, the term "fragment" or "segment" as applied to a protein or peptide, refers to a subsequence of a larger protein or peptide. A "fragment" or "segment" of a protein or peptide can be at least about 20 amino acids in length; for example at least about 50 amino acids in length; more preferably at least about 100 amino acids in length, even more preferably at least about 200 amino acids in length, particularly preferably at least about 300 amino acids in length, and most preferably at least about 400 amino acids in length.

As used herein, the term "gene" refers to an element or combination of elements that are capable of being expressed in a cell, either alone or in combination with other elements. In general, a gene comprises (from the 5' to the 3' end): (1) a promoter region, which includes a 5' nontranslated leader sequence capable of functioning in any cell such as a prokaryotic cell, a virus, or a eukaryotic cell (including transgenic animals); (2) a structural gene or polynucleotide sequence, which codes for the desired protein; and (3) a 3' nontranslated region, which typically causes the termination of transcription and the polyadenylation of the 3' region of the RNA sequence. Each of these elements is operably linked by sequential attachment to the adjacent element. A gene comprising the above elements is inserted by standard recombinant DNA methods into a plant expression vector.

As used herein, "gene products" include any product that is produced in the course of the transcription, reverse-transcription, polymerization, translation, post-translation and/or expression of a gene. Gene products include, but are not limited to, proteins, polypeptides, peptides, peptide fragments, or polynucleotide molecules.

As used herein, "homology" is used synonymously with "identity."

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

"Isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

"Neutralize," as used herein, means to inhibit the biological activity of a botulinum neurotoxin. Preferably, "neutralize," as used herein with respect to a botulinum neurotoxin, means to reduce or inhibit progression of a botulinum neurotoxin exposure in a subject or to reduce or prevent progression in a subject at risk of exposure to a botulinum neurotoxin. Preferred antibodies of this invention act to neutralize (reduce or eliminate) the toxicity of botulinum neurotoxin.

A "nucleic acid" refers to a polynucleotide and includes poly-ribonucleotides and poly-deoxyribonucleotides.

The term "oligonucleotide" typically refers to short polynucleotides of about 50 nucleotides or less in length. It will be understood that when a nucleotide sequence is represented herein by a DNA sequence (e.g., A, T, G, and C), this also includes the corresponding RNA sequence (e.g., a, u, g, c) in which "u" replaces "T".

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids which can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptide, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, anti-sense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences, provided that such changes in the primary sequence of the gene do not alter the expressed peptide ability to elicit passive immunity.

"Pharmaceutically acceptable" means physiologically tolerable, for either human or veterinary applications.

As used herein, "pharmaceutical compositions" include formulations for human and veterinary use.

A "preventive" or "prophylactic" treatment is a treatment administered to a subject who does not exhibit signs, or exhibits only early signs, of botulinum neurotoxin exposure or infection of *C. botulinum*. A prophylactic or preventative treatment is administered for the purpose of decreasing the risk of developing pathology associated with botulinum neurotoxin exposure or infection of *C. botulinum*.

"Botulinum neurotoxin or *C. botulinum*-associated disorder," as used herein, refers to a disorder in which there is an association between the presence of botulinum neurotoxin exposure or infection of *C. botulinum* and clinical signs thereof.

"Botulinum neurotoxin-neutralizing," as used herein with respect to recombinant human antibodies, refers to an antibody or mixture of antibodies which exhibits the ability to reduce the extent to which a botulinum neurotoxin exposure or infection of *C. botulinum* elicits a disease/disorder state in an animal. "Botulinum neurotoxin-neutralizing" is used interchangeably with "*C. botulinum-neutralizing* activity."

A "sample," as used herein, refers to a biological sample from a subject, including normal tissue samples, blood, saliva, feces, or urine. A sample can also be any other source of material obtained from a subject which contains a compound or cells of interest.

As used herein, an antibody "specifically binds," referring to an antibody binding to Botulinum neurotoxin, means that the antibody binds a Botulinum neurotoxin polypeptide, or fragment thereof, but does not bind to a non-Botulinum neurotoxin polypeptide. Antibodies that specifically bind to a Botulinum neurotoxin, or fragment thereof, do not cross-react with antigens outside of the family of Botulinum neurotoxins.

A "subject," as used herein, can be a human or non-human animal. Non-human animals include, for example, livestock and pets, such as ovine, bovine, porcine, canine, feline and murine mammals, as well as reptiles, birds and fish. Preferably, the subject is a human.

"Substantially purified" refers to a peptide or nucleic acid sequence which is substantially homogenous in character due to the removal of other compounds (e.g., other peptides, nucleic acids, carbohydrates, lipids) or other cells originally present. "Substantially purified" is not meant to exclude artificial or synthetic mixtures with other compounds, or the presence of impurities which do not interfere with biological activity, and which may be present, for example, due to incomplete purification, addition of stabilizers, or formulation into a pharmaceutically acceptable preparation.

"Synthetic mutant" includes any purposefully generated mutant or variant protein or nucleic acid. Such mutants can be generated by, for example, chemical mutagenesis, polymerase chain reaction (PCR) based approaches, or primer-based mutagenesis strategies well known to those skilled in the art.

The terms to "treat" or "treatment," as used herein, refer to administering botulinum neurotoxin-neutralizing antibodies or compounds to reduce the frequency with which the effects or symptoms of a botulinum neurotoxin exposure or *C. botulinum* infection are experienced, to reduce the severity of symptoms, or to prevent effects or symptoms from occurring.

The term "vaccine" as used herein is defined as a material used to provoke an immune response after administration of the material to a mammal. For example, a botulinum neurotoxin vaccine would comprise a molecule derived from botulinum neurotoxin that when administered to a mammal elicits an immune response in the mammal.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine, and the like.

DESCRIPTION OF THE FIGURES

FIGS. 1A and 1B is chart showing the expression of hTERT by each cell line as measured by RT-PCR; odd numbered lanes correspond to expression of hTERT; even lanes correspond to expression of GAPDH. FIG. 1A shows the expression of hTERT in the 6 subclones derived from the SP2/mL-6 MPT cell line (lanes 1-12 depict the 6 subclones; lanes 13-14 depict the K6H6/B5 cell line; lanes 15-16 depict the B5-6T cell line). FIG. 1B shows the expression of hTERT by the subclones derived from the B5-6T cell line (lanes 1-12 depict the subclones of the B5-6T cell line; lanes 13-14 B5-6T; lanes 15-16 depict the K6H6/B5 cell line).

FIG. 3, comprising FIG. 3A is a chart demonstrating that the average association rate constant ($k_{on}$) value for 13A. The $k_{on}$ value was determined by mixing HC50A (200 pM) with 13A (10 pM) and sampling the free antibody concentration over time. Representative data plotted to a general bimolecular association model to give an average $k_{on}$ value of $7.2 \times 10^6$ $M^{-1}$ $s^{-1}$. FIG. 3B is a chart depicting the binding properties of the 13A antibody to HC50A as measured by a kinetic exclusion assay. The equilibrium binding affinity was determined by titrating HC50A into solutions containing 13A (1 nM, 0.1 nM). The data were plotted on a single-site binding model to give an optimized KD value of $9.7 \times 10^{-11}$ M.

FIG. 4, comprising FIGS. 4A and 4B, is a chart depicting the amino acid and nucleic acid sequences of the heavy and light chain variable domains of the botulinum neurotoxin 13A antibody.

DETAILED DESCRIPTION OF THE INVENTION

Figure 1:
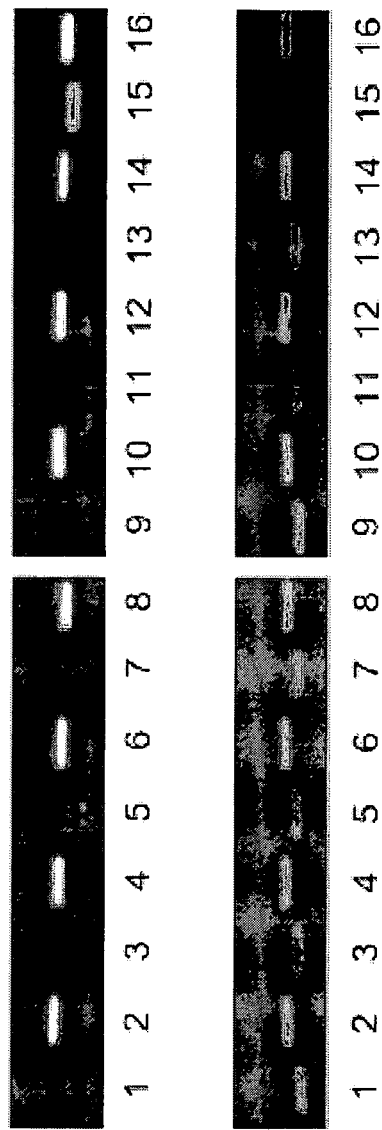
FIG. 1, comprising

A cell line designated "B5-6T" is provided. The cell line is useful as a fusion partner for fusion to B-lymphocytes in producing hybridomas that produce monoclonal antibodies. The B5-6T cell line was deposited under the terms of the Budapest Treaty with the American Type Culture Collection, 10801 University Blvd, Manassas, Va. 20110-2209, USA, on Jan. 15, 2008 and assigned ATCC Accession No. PTA-8869.

Provided are hybridomas resulting from the fusion between the B5-6T fusion partner cell line with a B-lymphocytec and antibodies secreted from the hybridoma. Preferably, the B-lymphocyte is derived from a human, and the antibody secreted from the hybridoma is a human monoclonal antibody. One such hybridoma is ATCC PTA-8871 that produces an antibody that binds to and neutralizes BoNT/A.

Monoclonal antibody production proceeds by exposing a human or a non-human animal with an immunogen (e.g., the pentavalent botulinum neurotoxin vaccine). The animal is then sacrificed and the cells are taken from the spleen of the animal. Preferably, B-lymphocytes are obtained from peripheral blood or other sites of the animal. The B-lymphocytes are cultured in vitro and can be stimulated with a mitogen, such as pokeweed mitogen, prior to fusion the B5-6T fusion partner cell line. The result is a population of hybridomas that are capable of reproducing in vitro. The population is then screened to isolate individual clones, each of which secretes a single antibody species that binds the immunogen. In this manner, the individual antibody species obtained from the hybridoma is derived from a B-lymphocyte resulting from an immune response in the immunized animal. Thus, the monoclonal antibody recognizes a specific target on the immunogen.

Fusion Partner

The B5-6T fusion partner cell line can be used as a fusion partner for fusion with any B-lymphocyte. For example, the fusion partner may be fused to a human B-lymphocyte to produce a stable hybridoma. In one embodiment, the fusion partner may be fused to a human B-lymphocyte isolated from an immunized human to produce a plurality of hybridomas. The hybridomas can be screened to select a hybridoma producing a monoclonal antibody of interest, and cultured to produce the antibody.

The stable expression of hTERT in the B5-6T fusion partner cell line is an improvement over other fusion partners known in the art. It has been observed that fusion partner cell lines in the art loss ectopic expression of hTERT after a period of continuous culturing. The inability of prior art fusion partner cell lines to maintain ectopic expression of hTERT contributes to the inefficiencies of using those fusion partner cell lines for forming human antibody-secreting hybridomas. The hybridomas formed between prior art fusion partner cells and human B-lymphocytes also suffer from inadequate hTERT expression and therefore are inferior to hybridomas formed from using the B5-6T fusion partner cell line.

An advantage of using the B5-6T fusion partner cell line over cells in the art is that the B5-6T fusion partner cell line allows for the generation of hybridomas at an increased frequency. A characteristic of the B5-6T fusion partner cell line is the ability for the cell line to fuse with B-lymphocytes and produce hybridomas capable of surviving HAT selection at a highly efficient rate. For example, the number of hybridoma colonies resulting from a fusion of B5-6T fusion partner cells and primary B-lymphocytes is greater than 2-fold higher than that resulting from the fusion of SP2/mIL-6/MPT or K6H6/B5 cells of the prior art and primary B-lymphocytes (FIG. 2).

Figure 2:
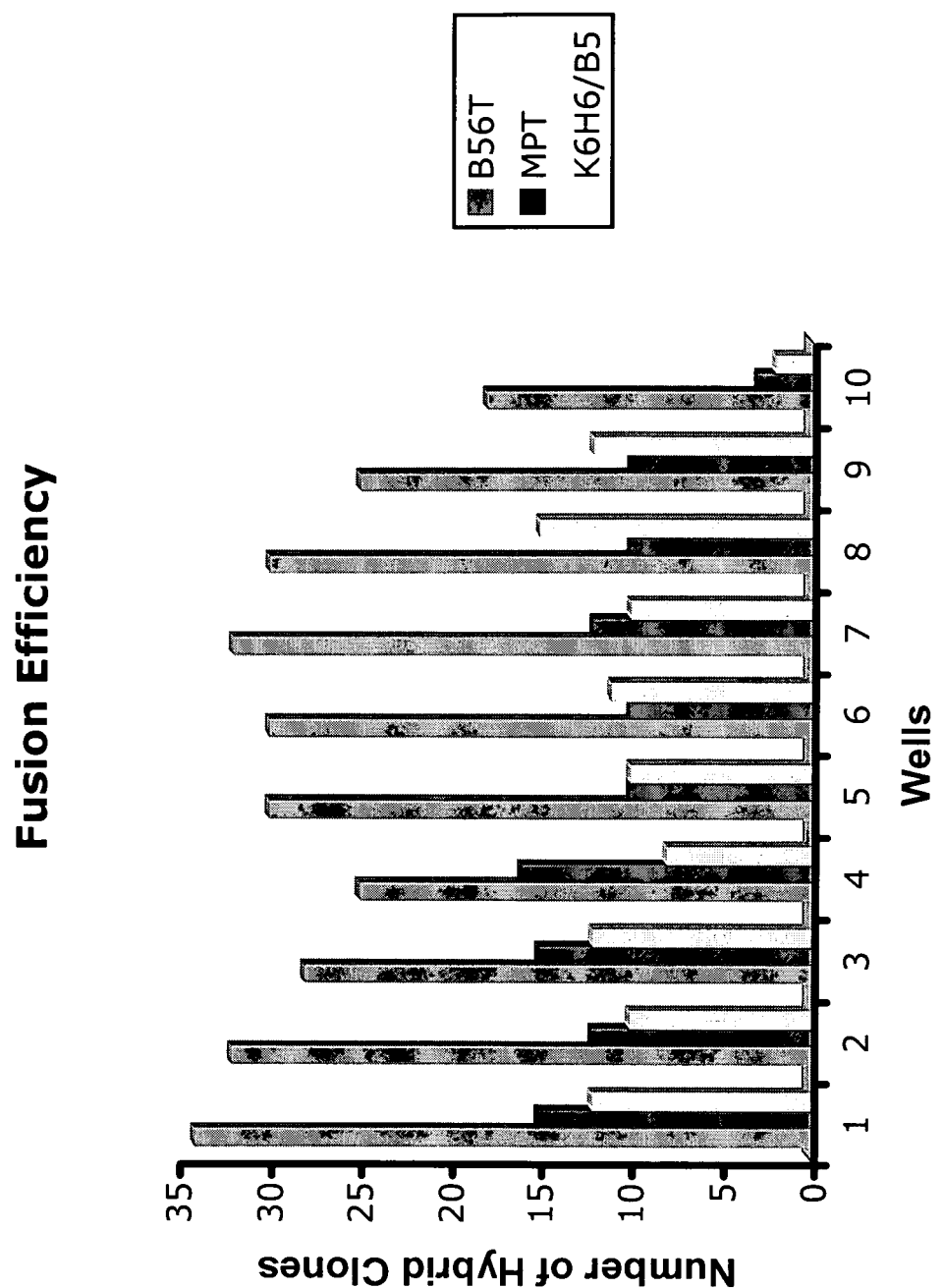
FIG. 2 is a chart demonstrating the fusion efficiency of the three different fusion partner cell lines, MPT, K6H6/B5, and B5-6T. Peripheral blood lymphocytes were fused with each fusion partner cell line. The fusion efficiency is counted as the number of clones in each well.

Adding the total number of clones produced by the three different fusion partner cell lines in the experiment shown in FIG. 2, following fusion with equivalent numbers of B-cells, the total number of hybrid clones arising from the B5-6T cell line was 284, compared to 113 clones from the SP2/mIL-6 MPT cell line and 102 clones from the K6H6/B5 cell line.

The fusion partner of the invention is also characterized by an ability to produce hybridomas that are stable (i.e., hybridomas that maintain the ability to produce a particular antibody for an extended time periods, e.g., at least three rounds of culturing in vitro). In other words, a monoclonal-antibody producing hybridoma cell line produced using the B5-6T fusion partner cell line can be subcloned and subcultured for many passages, until sufficient numbers of cells are obtained to produce antibodies in gram quantities or greater.

Another advantage of using the B6-6T fusion partner cell line is that hybridomas generated therefrom are able to be adapted to culturing conditions that are serum-free. The ability to culture the hybridoma in a serum free medium overcomes complications associated with isolating and purifying antibodies from a culture medium that contains serum.

B5-6T Cell Line for Generating Human Antibodies

Hybridomas can be generated by the fusion of the B5-6T fusion partner cell line with human B-lymphocytes at an unexpected high frequency compared to the number of hybridomas generated using known prior art fusion partners. In addition, the hybridoma clones secrete immunoglobulin for a longer amount of time in culture compared to clones generated from other fusion partners.

The B5-6T fusion partner cell line can be used in any standard method of generating a hybridoma. For example, the B5-6T cell line can be fused with any B lymphocyte. B lymphocytes can be obtained from an individual, preferably from tissue selected from the group consisting of peripheral blood, bone marrow, cord blood, lymph nodes, Peyer's patches, spleen, tumor samples, and sites of infection. In some aspects, the individual has been exposed to an infectious agent or an antigen thereof. The infectious agent includes, but are not limited to viruses, bacteria, fungi, and prions. Preferably, the individual has elicited an immune response against the antigen.

In other aspects, B lymphocytes are isolated from an individual who has been exposed to a tumor or an antigen thereof. The tumor preferably is a solid tumor selected from the group consisting of a gastrointestinal tumor, a breast tumor, a kidney tumor, a brain tumor, a liver tumor, a stomach tumor, a lung tumor, a pancreatic tumor, a tumor of the reproductive systems, a prostate tumor, an eye tumor, a skin tumor, a melanoma, adenomas, polyps, dysplasias, in situ carcinoma, and intra-epithelial neoplasm. In other aspects, the tumor is a hematopoietic tumor selected from the group consisting of leukemia, lymphoma, myeloma, and myelodysplastic syndromes. Preferably, the individual has developed an immune response against the self-antigen.

Accordingly, the method of producing a hybridoma using the B5-6T fusion partner cell line can be used to produce any desirable antibody. As an example, antibodies specific for the botulinum neurotoxin is discussed, but the invention should not be limited to only these antibodies. Antibodies specific for botulinum neurotoxin can be generated using the methods disclosed herein, wherein B-lymphocytes are isolated from a human immunized against a selected antigen such as BoNT polypeptide (e.g., BoNT/A). The B-lymphocytes are obtained from the spleen, blood or lymph nodes of the human donor. If antibodies against a specific antigen or epitope are desired, it is preferable to use that antigen or epitope thereof as the immunogen rather than the entire polypeptide. Alternatively, B-lymphocytes are obtained from an unimmunized individual and stimulated with the immunogenic polypeptide, or a epitope thereof, in vitro. In a further variation, B-lymphocytes are obtained from an infected, or otherwise immunized individual, and then hyperimmunized by exposure to an immunogenic polypeptide for a period of time in vitro. In some instances, the B-lymphocytes are further cultured in the present of pokeweed mitogen for a period of time prior to fusing the pokeweed mitogen stimulated B-lymphocytes with the B5-6T fusion partner cell line.

The immunized B-lymphocytes prepared by one of the above procedures can be fused with the B5-6T fusion partner cell line by well known methods. For example, the cells are treated with 40-50% polyethylene glycol of MW 1000-4000, at about 37° C. for about 5-10 minutes. Cells are separated from the fusion mixture and propagated in media selective for the desired hybrids. When the hybrid cell is resistant to 8-azaguanine, the cell is conveniently selected by successive passaging of the cell on HAT or AH medium. This selection process allows for the selection of viable hybridomas. Other selective procedures can be used depending on the nature of the cells used in fusion. Clones secreting antibodies having the required binding specificity are identified by assaying the antibody secreted into the culture medium for the ability to bind to the botulinum neurotoxin polypeptide or an epitope thereof. The antibody producing cells having the desired specificity are subcloned by the limiting dilution technique and grown in vitro in culture medium, or are injected into selected host animals and grown in vivo.

The antibodies produced from the hybridomas are then tested for the ability to bind the immunogen or an epitope thereof. Antibodies are separated from the resulting culture medium by conventional antibody-fractionation procedures, such as ammonium sulfate precipitation, DEAE cellulose chromatography, and affinity chromatography. An advantage of using the B5-6T fusion partner cell line for the generation of a hybridoma is that the hybridoma can be adapted to be cultured in a serum free medium. Isolating antibodies from a serum free medium overcomes complications associated with isolating antibodies in a medium containing serum. For example, serum contains antibodies. Thus, culturing hybridomas in a serum free medium decreases the amount of contaminants present in serum. According, antibody samples isolated from a serum free medium are more pure than antibody samples isolated from a medium containing serum.

Antibodies

In one embodiment, the invention is directed to a human anti-BoNT/A-binding antibody. The antibody comprises a heavy chain polypeptide comprising an antibody heavy chain variable domain comprising the amino acid sequence of SEQ ID NO: 4, and an antibody light chain polypeptide comprising and antibody light chain variable domain comprising the amino acid sequence SEQ ID NO: 8. The aforementioned amino acid sequences constitute the light and heavy chain polypeptides of the antibody secreted by hybridoma ATCC PTA-8871. The aforementioned amino acid sequences also constitute the light and heavy chain polypeptides of the 13A antibody.

In another embodiment, the invention is directed to a human anti-BoNT/A-binding antibody comprising a heavy chain polypeptide comprising the amino acid sequence of SEQ ID NO: 3, and an antibody light chain polypeptide comprising the amino acid sequence SEQ ID NO: 7. The aforementioned amino acid sequences constitute the light and heavy chain polypeptides of the antibody secreted by hybridoma ATCC PTA-8871. The aforementioned amino acid sequences also constitute the light and heavy chain polypeptides of the 13A antibody.

In another embodiment, the antibody specifically binds to an epitope specifically bound by the 13A antibody. In another embodiment, the antibody comprises the 13A antibody. In a further embodiment, antigen-binding fragments are provided.

The antibodies produced may be tested for the ability to bind BoNT/A or an epitope thereof. Antibodies may also be tested for the capacity to neutralize BoNT/A neurotoxin. Toxicity can be determined in vivo. For example, one can measure the toxicity of BoNT/A in a test animal (e.g. mouse) in the presence of one or more putative neutralizing antibodies. A neutralizing antibody can be combined with the botulinum neurotoxin prior to administration, or the animal can be administered with the antibody prior to, simultaneous with, or after administration of the neurotoxin.

A preferred in vitro assay for neutralizing activity uses a hemidiaphragm preparation (Deshpande et al., 1995, Toxicon 33:551-557). Briefly, purified antibodies are incubated with purified BoNT/A for 30 minutes at room temperature and then added to the tissue bath, resulting in a final antibody concentration of about $2.0 \times 10^{-8}$ M and a final neurotoxin concentration of about $2.0 \times 10^{-11}$ M. For each antibody studied, time to 50% twitch tension reduction is determined (e.g., three times for BoNT/A). Differences between times to a given (arbitrary) percentage (e.g. 50%) twitch reduction are determined by standard statistical analyses (e.g. two-tailed t test) at standard levels of significance (e.g., a P value of <0.05 considered significant).

Preferred antibodies of this invention act to neutralize (reduce or eliminate) the toxicity of botulinum neurotoxin (e.g. botulinum neurotoxin type A). In vivo neutralization measurements involve measuring changes in the lethality (e.g. $LD_{50}$ or other standard metric) due to a botulinum neurotoxin (e.g. botulinum neurotoxin type A) administration due to the presence of one or more antibodies being tested for neutralizing activity. The neurotoxin can be directly administered to the test organism (e.g. mouse) or the organism can harbor a botulism infection (e.g., be infected with *Clostridium botulinum*). The antibody can be administered before, during, or after the injection of BoNT/A neurotoxin or infection of the test animal. A decrease in the rate of progression, or mortality rate indicates that the antibody(s) have neutralizing activity.

The BoNT/A antibodies of the invention are useful in the treatment of pathologies associated with botulinum neurotoxin poisoning. The treatments essentially comprise administering to the poisoned animal (e.g. human or non-human mammal) a quantity of BoNT/A neutralizing antibody sufficient to neutralize (e.g. mitigate or eliminate) symptoms of botulinum neurotoxin poisoning.

Such treatments are most desired and efficacious in acute cases, such as where vital capacity is less than 30-40 percent of predicted and/or paralysis is progressing rapidly and/or hypoxemia with absolute or relative hypercarbia is present. Treatment with a neutralizing antibody can be provided as a adjunct to other therapies (e.g. antibiotic treatment).

Modification of Antibodies

The invention includes antibodies that specifically bind to an epitope specifically bound by the 13A antibody. The invention includes functional equivalents of the 13A antibody described herein. Functional equivalents have binding characteristics comparable to those of the 13A antibody, and include, for example, hybridized and single chain antibodies, as well as fragments thereof. Methods of producing such functional equivalents are disclosed in PCT Application WO 93/21319 and PCT Application WO 89/09622.

Functional equivalents of the 13A antibody further include antibodies or fragments thereof that have the same, or substantially the same, binding characteristics to those of the whole antibody. Such fragments may contain one or both Fab fragments or the F(ab')$_2$ fragment. Preferably the antibody fragments contain all six complement determining regions of the whole antibody, although fragments containing fewer than all of such regions, such as three, four or five complement determining regions, are also functional. The functional equivalents are members of the IgG immunolglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Preferred constant regions are gamma 1 (IgG1), gamma 2 (IgG2 and IgG), gamma 3 (IgG3) and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H$_2$L$_2$) formed of two dimers associated through at least one disulfide bridge.

A) Phage Display

A phage display can be used to increase antibody affinity. To create antibodies of higher affinity for a botulinum toxin, for instance a BoNT/A-bind antibody, mutant single chain variable fragment (scFv) gene repertoires, based on the sequences disclosed herein can be created and expressed on the surface of phage. For a BoNT/A-binding antibody, mutant scFv gene repertoires based on the variable domains of antibody 13A are prepared. Display of antibody fragments on the surface of viruses which infect bacteria (bacteriophage or phage) makes it possible to produce human or other mammalian antibodies with a wide range of affinities and kinetic characteristics. To display antibody fragments on the surface of phage (phage display), an antibody fragment gene is inserted into the gene encoding a phage surface protein and the antibody fragment-fusion protein is expressed on the phage surface (McCafferty et al., 1990, Nature 348: 552-554; Hoogenboom et al., 1991, Nucleic Acids Res. 19:4133-4137).

Since the antibody fragments on the surface of the phage are functional, those phage bearing antigen binding antibody fragments can be separated from non-binding or lower affinity phage by antigen affinity chromatography (McCafferty et al., 1990, Nature 348:552-554). Mixtures of phage are allowed to bind to the affinity matrix, non-binding or lower affinity phage are removed by washing, and bound phage are eluted by treatment with acid or alkali. Depending on the affinity of the antibody fragment, enrichment factors of 20 fold-1,000,000 fold are obtained by single round of affinity selection.

One approach for creating mutant scFv gene repertoires involves replacing either the V$_H$ or V$_L$ gene from a binding scFv with a repertoire of V$_H$ or V$_L$ genes (otherwise known as chain shuffling) (Clackson et al., 1991, Nature 352:624-628). Such gene repertoires contain numerous variable genes derived from the same germline gene as the binding scFv, but with point mutations (Marks et al., 1992, Biotechnology 10:779-783). Using light or heavy chain shuffling and phage display, the binding avidities of BoNT/A-binding antibody fragment can be dramatically increased.

In order to generate an antibody having an increased affinity, during the screening for the antibody, the antigen concentration is decreased in each round of selection, reaching a concentration less than the desired K$_d$ by the final rounds of selection. This results in the selection of a desired antibody on the basis of affinity (Hawkins et al., 2002, J. Mol. Biol. 226: 889-896).

B) Site Directed Mutagenesis

To generate a BoNT/A-binding antibody, site directed mutagenesis is based on the variable domains of the antibody 13A. It is well known in the art that mutating amino acids that contact ligand has been shown to be an effective means of increasing the affinity of one protein molecule for its binding partner (Lowman et al., 1993, J. Mol. Biol. 234:564-578; Wells, 1990, Biochemistry 29:8509-8516). The majority of antigen-contacting, amino acid side chains in an antibody are located in the complementarity determining regions (CDRs). Three of the CDRs occur in the V$_H$ (CDR1, CDR2, and CDR3) and three in the V$_L$ (CDR1, CDR2, and CDR3) (Chothia et al., 1987, J. Mol. Biol. 196:901-917; Chothia et al., 1986, Science 233:755-8; Nhan et al., 1991, J. Mol. Biol. 217:133-151). These residues contribute the majority of binding energetics responsible for antibody affinity for antigen.

The CDRs are separated by framework regions. The framework regions spatially orient the CDR regions to shape the antigen-binding structure. Mutations to residues in either CDR regions or framework regions may alter and/or improve the binding characteristics of an antibody. Due to their structural role, changes to residues in framework regions may result in improperly folded antibody structures that may be inactive (Shlomchik et al, 1989, Prog Immunol. 7:415-423). Consequently, changes to framework region residues should be conservative changes and should preserve hydrophobic packing interactions and buried salt bridges. The determination of which amino acids in an immunoglobulin protein sequence contribute to which domains is well understood in the art. See Lefranc et al., (2005, Nucleic Acids Res 33:D593-D597).

CDR and FR residues are determined according to a standard sequence definition (Kabat et al., Sequences of Proteins of Immunological Interest, National Institutes of Health, Bethesda Md. (1987), and a structural definition (as in Chothia and Lesk, J. Mol. Biol. 196:901-917 (1987). Where these two methods result in slightly different identifications of a CDR, the structural definition is preferred, but the residues identified by the sequence definition method are considered important FR residues for determination of which framework residues to import into a consensus sequence.

Accordingly, mutation of the CDRs and screening of the resulting mutants against BoNT/A or the epitopes thereof identified herein, may be used to generate BoNT/A-binding antibodies having improved binding affinity to an epitope and/or bind with higher affinity to specific sub-serotypes (Smith et al., 2005, Infect. Immun. 73:5450-5457).

In a preferred embodiment, each CDR is randomized in a separate library. To simplify affinity measurements, existing antibodies or other lower affinity BoNT/A-binding antibodies, are used as a template, rather than a higher affinity scFv. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al., 1993, J. Mol. Biol., 234:564-578).

To increase the affinity of BoNT/A-binding antibodies, amino acid residues located in one or more CDRs (e.g. 9 amino acid residues located in $V_L$ CDR3) are partially randomized by synthesizing a "doped" oligonucleotide in which the wild type nucleotide occurred with a frequency of about for example 49%. The oligonucleotide is used to amplify the remainder of the BoNT/A-binding scFv gene(s) using PCR.

For example, in one embodiment, to create a library in which $V_H$ CDR3 is randomized, an oligonucleotide is synthesized which anneals to the BoNT/A-binding antibody $V_H$ framework 3 and encodes $V_H$/CDR3 and a portion of framework 4. At the four positions to be randomized, the sequence "NNS" can be used, where N is any of the 4 nucleotides, and S is "C" or "T". The oligonucleotide is used to amplify the BoNT/A-binding antibody $V_H$ gene using PCR, creating a mutant BoNT/A-binding antibody $V_H$ gene repertoire. PCR is used to splice the $V_H$ gene repertoire with the BoNT/A-binding antibody light chain gene, and the resulting scFv gene repertoire is cloned into a phage display vector. Ligated vector DNA is used to transform electrocompetent *E. coli* to produce a phage antibody library.

To select higher affinity mutant scFv, each round of selection of the phage antibody libraries is conducted on decreasing amounts of BoNT/A, as described elsewhere herein. Typically, 96 clones from the third and fourth round of selection are screened for binding to the BoNT/A antigen by ELISA on 96 well plates.

Other methods known in the art and used for mutagenizing antibodies include error-prone PCR, over-expression of dominant-negative mismatch repair proteins (WO 2004/046330), parsimonius mutagenesis (Razai et al., 2005, J Mol. Biol. 351:158-169) and chemical mutagenesis. See also: Chowdhury et al (2005, Methods 36:11-27) and Carter (2006, Nat Rev Immunol. 6:343-357). Identification of antibodies with desirable properties can be achieved using a variety of common screenin methods (Hoogenboom, 2005, Nat. Biotechnol. 23:1105-1116).

C) Creation of Botulinum Neurotoxin-Binding (scFv')$_2$ Homodimers

To create botulinum neurotoxin-binding (scFv')$_2$ antibodies, two botulinum neurotoxin-binding scFvs are joined, either through a linker (e.g., a carbon linker, a peptide, etc.) or through a disulfide bond between, for example, two cysteines. Thus, for example, to create disulfide linked botulinum neurotoxin-binding scFv, a cysteine residue can be introduced by site directed mutagenesis.

In a particularly preferred embodiment, the (scFv')$_2$ dimer is created by joining the scFv fragments through a linker, more preferably through a peptide linker. This can be accomplished by a wide variety of means well known to those of skill in the art. For example, one preferred approach is described by Holliger et al., 1993, Proc. Natl. Acad. Sci. USA 90:6444-6448 (see also WO 94/13804).

Typically, linkers are introduced by PCR cloning. For example, synthetic oligonucleotides encoding the linker can be used to PCR amplify the BoNT/A-binding antibody $V_H$ and $V_L$ genes which are then spliced together to create the BoNT/A-binding diabody gene. The gene is then cloned into an appropriate vector, expressed, and purified according to standard methods well known to those of skill in the art.

D) Preparation of Botulinum Neurotoxin-Binding (scFv)$_2$, Fab, and (Fab')$_2$ Molecules BoNT/A-binding antibodies, such as a BoNT/A-binding scFv, or variant(s) with higher affinity, are suitable templates for creating size and valency variants. For example, a BoNT/A-binding (scFv')$_2$ is created from a parent scFv derived from the variable domains of antibody 13A, as described above. An scFv gene can be excised using appropriate restriction enzymes and cloned into another vector.

A botulinum neurotoxin-binding Fab is expressed in *E. coli* using an expression vector similar to the one described by Better et. al., 1988, Science 240:1041-1043. To create a BoNT/A-binding Fab, the $V_H$ and $V_L$ genes are amplified from the scFv using PCR. The $V_H$ gene is cloned into an expression vector (e.g., a PUC119 based bacterial expression vector) that provides an IgG $C_{H1}$ domain downstream from, and in frame with, the $V_H$ gene. The vector also contains a leader sequence to direct expressed $V_H$-$C_{H1}$ domain into the periplasm, a leader sequence to direct expressed light chain into the periplasm, and cloning sites for the light chain gene. Clones containing the correct VH gene are identified, e.g., by PCR fingerprinting. The $V_L$ gene is spliced to the $C_L$ gene using PCR and cloned into the vector containing the $V_H C_{H1}$ gene.

Genetic Modification

In addition to obtaining botulinum neurotoxin-binding antibodies from a hybridoma, the antibodies can also be generated by cloning antibody genes into one or more expression vectors, and transforming the vector into a cell line such as the cell lines typically used for expression of recombinant or humanized immunoglobulins.

The genes encoding the heavy and light chains of immunoglobulins secreted by the cell lines are cloned according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al., 1992, J. Immunol. 148:1149). For example, genes encoding heavy and light chains are cloned from the antibody secreting cell's genomic DNA or cDNA is produced by reverse transcription of the cell's RNA. Cloning is accomplished by conventional techniques including the use of PCR primers that hybridize to the sequences flanking or overlapping the genes, or segments of genes, to be cloned.

Nucleic acids encoding the heavy and light chains of the antibodies or portions thereof can be obtained and used in accordance with recombinant DNA techniques for the production of the specific immunoglobulin, immunoglobulin chain, or variants thereof, in a variety of host cells or in an in vitro translation system. For example, the nucleic acids, including cDNAs, or derivatives thereof encoding variants such as a the heavy and light chains, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

The heavy and light chains, or portions thereof, can be assembled in two different expression vectors that can be used to cotransfect a recipient cell. Each vector can contain two selectable genes, one for selection in a bacterial system and one for selection in a eukaryotic system. These vectors allow for the production and amplification of the genes in bacterial systems, and subsequent cotransfection of eukaryotic cells and selection of the cotransfected cells. The selection procedure can be used to select for the expression of immunoglobulin chain genes introduced on two different DNA vectors into a eukaryotic cell.

Alternatively, the genes encoding a heavy chain and light chain may be expressed from one vector. Although the light and heavy chains are coded for by separate genes, they can be joined, using recombinant methods. For example, the two polypeptides can be joined by a synthetic linker that enables them to be made as a single protein chain in which the VL and VH regions pair to form monovalent molecules (known as single chain Fv (scFv); see e.g., Bird et al., 1988, Science 242: 423-426; and Huston et al., 1988, Proc. Natl. Acad. Sci. USA 85: 5879-5883).

The invention provides for an isolated nucleic acid molecule comprising a nucleic acid sequence encoding at least a heavy and a light chain variable region. A nucleic acid molecule comprising sequences encoding both the light and heavy chain variable regions can be engineered to contain a synthetic signal sequences for secretion of the immunoglobulin chains when produced in a cell. Furthermore, the nucleic acid molecule comprising both the heavy and light chain variable regions can contain specific DNA links which allow for the insertion of other immunoglobulin sequences and maintain the translational reading frame so to not alter the amino acids normally found in immunoglobulin chains. In particular, the nucleic acid molecule comprises sequences that encode the heavy chain variable domain comprising the amino acid sequence SEQ ID NO: 4 and the antibody light chain variable domain comprising the amino acid sequence SEQ ID NO: 8. In another aspect, the nucleic acid molecule comprises sequences of SEQ ID NO: 2 and SEQ ID NO: 6.

The invention also provides for an isolated nucleic acid molecule comprises sequences that encode the heavy chain polypeptide comprising the amino acid sequence SEQ ID NO: 3 and the antibody light chain polypeptide comprising the amino acid sequence SEQ ID NO: 7. In another aspect, the nucleic acid molecule comprises sequences of SEQ ID NO: 1 and SEQ ID NO: 5.

In accordance with the present invention, nucleotide sequences coding for heavy and light chains may be inserted into an appropriate expression vector. This vector which contains the necessary elements for transcription and translation of the inserted protein-coding sequence so as to generate recombinant DNA molecules that direct the expression of heavy and light chain immunoglobulins for the formation of an antibody.

In addition to the DNA segments encoding BoNT/A-binding immunoglobulins or fragments thereof, other substantially homologous modified immunoglobulins can be readily designed and manufactured utilizing various recombinant DNA techniques known to those skilled in the art such as site-directed mutagenesis. Such modified segments will usually retain antigen binding capacity and/or effector function. Moreover, the modified segments are usually not so far changed from the original genomic sequences of the antibody producing cell to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

A variety of methods can be used to express genes in a cell. Nucleic acids can be cloned into a number of types of vectors. However, the present invention should not be construed to be limited to any particular vector. Instead, the present invention should be construed to encompass a wide plethora of vectors which are readily available and/or well-known in the art. For example, an the nucleic acid of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Viral vector technology is well known in the art and is described, for example, in Sambrook et al. (1989), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. Preferably, a murine stem cell virus (MSCV) vector is used to express a desired nucleic acid. MSCV vectors have been demonstrated to efficiently express desired nucleic acids in cells. However, the invention should not be limited to only using a MSCV vector, rather any retroviral expression method is included in the invention. Another example of a viral vector is a Moloney Murine Leukemia Virus (MoMuLV) vector. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Retroviral vectors have been used extensively to deliver genes into a host cell or animal. Retroviral integration can take place at many locations. Retroviral insertion biases have been estimated by a variety of methods reviewed in Uren et al., 2005 Oncogene 24: 7656-7672. There is evidence that there is a preference for integration close to DNAseI sensitive and/or hypomethylated regions suggesting that retroviral integration has a tendency to insert within actively transcribed regions of the genome. Other evidence suggests that retroviral integration preferentially occurs near gene promoters. Generally, the evidence suggests that retroviral integration is correlated with the target DNA's local characteristics, including conformation and methylation status, gene density, chromatin conformation, host DNA associated proteins and local transcriptional activity. Accordingly, retroviral integration is partially affected by nucelosome structure rather than any particular sequence specificity. Thus, the integration site is unpredictable.

For expression of the desired gene, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (1989). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the desired gene(s), the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. and Ausubel et al.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The preparation and use of such systems is well known in the art.

Regardless of the method used to introduce exogenous nucleic acids into a host cell or otherwise expose a cell to the nucleic acid of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Cells that have undergone alteration of their DNA in order to cause such ectopic expression can be identified by single cell cloning and analyzing genomic DNA of the cloned cells for the presence of the altered DNA sequences using PCR with primers specific for the altered DNA sequences.

Cells that have integrated an ectopic gene into the genome of a cell can be identified by single cell cloning and analyzing genomic DNA of the cloned cells for the presence of the ectopic telomerase gene using PCR with primers specific for the altered DNA sequences. Expression of the ectopic gene can be confirmed with RT-PCR.

Therapeutic Use and Pharmaceutical Compositions

One skilled in the art can readily determine an effective amount of botulinum neurotoxin-neutralizing antibody to be administered to a given subject, by taking into account factors such as the size and weight of the subject; the extent of disease penetration; the age, health and sex of the subject; the route of administration; and whether the administration is regional or systemic. Generally, the amount of antibody administered to a subject depends upon the amount of botulinum neurotoxin that needs to be neutralized and the amount of botulinum neurotoxin-neutralizing activity exhibited by the antibodies. Those skilled in the art may derive appropriate dosages and schedules of administration to suit the specific circumstances and needs of the subject. For example, suitable doses of each antibody to be administered can be estimated from the amount of botulinum neurotoxin to which a subject has been exposed, or the amount of botulinum neurotoxin to which the subject is in risk of being exposed. Typically, dosages of antibody are between about 0.001 mg/kg and about 100 mg/kg body weight. In some embodiments, dosages are between about 0.01 mg/kg and about 60 mg/kg body weight.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

A mixture of botulinum neurotoxin-neutralizing human antibodies can be administered in equimolar concentrations to a subject in need of such treatment. In another instance, the antibodies are administered in concentrations which are not equimolar. In other instances, the antibodies are administered as equal amounts of protein, by weight, per kilogram of body weight. For example, the antibodies can be administered in equal amounts, based on the weight of the subject. In another instance, the antibodies are administered in unequal amounts. In yet other instances, the amount of each antibody to be administered is based on its neutralizing activity. For example, a mixture with between about 1 IU/kg body weight and about 50 IU/kg body weight of botulinum neurotoxin-neutralizing activity can be administered.

In general, the schedule or timing of administration of a mixture of botulinum neurotoxin-neutralizing human antibodies is according to the accepted practice for the procedure being performed.

When used in vivo, the antibodies, either in their native form and/or in a recombinant form, are preferably administered as a pharmaceutical composition, comprising a mixture, and a pharmaceutically acceptable carrier. The antibodies may be present in a pharmaceutical composition in an amount from 0.001 to 99.9 wt %, more preferably from about 0.01 to 99.0 wt %, and even more preferably from 0.1 to 50 wt %. To achieve good plasma concentrations, an antibody, or a combination of antibodies, may be administered, for example, by intravenous injection, as a solution comprising 0.1 to 1.0% of the active agent.

The botulinum neurotoxin-neutralizing antibodies are useful for prophylactic and/or therapeutic treatment. The antibodies can be a component of a pharmaceutical composition. The pharmaceutical compositions of this invention are particularly useful for parenteral administration, such as intravenous administration or administration into a body cavity or lumen of an organ. The compositions for administration will commonly comprise a solution of botulinum neurotoxin-neutralizing antibody dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of botulinum neurotoxin-neutralizing in these formulations can vary widely, and will be selected primarily based on fluid volumes, viscosities, body weight and the like in accordance with the particular mode of administration selected and the subject's needs.

Thus, a typical pharmaceutical composition for intravenous administration would be about 0.1 to 10 mg per subject per day. Dosages from 0.1 up to about 100 mg per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., Mack Publishing Company, Easton, Pa. (1980).

The compositions containing the antibody of the present invention can be administered for therapeutic treatments. In therapeutic applications, preferred pharmaceutical compositions are administered in a dosage sufficient to neutralize (mitigate or eliminate) BoNT/A (e.g., reduce or eliminate a symptom of BoNT/A (botulism)). An amount adequate to accomplish this is defined as a "therapeutically effective dose." Amounts effective for this use will depend upon the severity of the disease and the general state of the subject's health.

Single or multiple administrations of the compositions may be administered depending on the dosage and frequency as required and tolerated by the subject. In any event, the composition should provide a sufficient quantity of the proteins of this invention to effectively treat the subject.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (e.g. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Expression of Ectopic Genes in Heteromyeloma Cell Line

The following experiments were designed to establish a fusion partner cell line that increases the frequency of generating hybridomas that stably express human immunoglobulin. The results presented herein demonstrate that the B5-6T fusion partner cell line, which ectopically co-expresses the genes encoding the murine interleukin-6 (mIL-6) and the human telomerase catalytic subunit (hTERT) genes, is able to generate desirable hybridomas at in increased frequency.

The mIL-6 gene was introduced into the K6H6/B5 heteromyeloma cell line (Carroll et al., 1986 J. Immunol. Methods 89: 61-72; CRL-1823, ATCC, Manassas, Va.) to ectopically express mIL-6 using the plasmid pMSCV puro mIL-6. Briefly, ectopic expression of mIL-6 in the K6H6/B5 cell line was achieved through infection of cells with replication-defective ectopic retroviruses using a protocol described previously (Hahn et al., 2002 Mol. Cell. Biol. 22: 2111). K6H6/B5 cells infected with the pMSCV puro mIL-6 retrovirus were cloned and a cell line expressing high levels of mIL-6 was isolated. A polyclonal population of mIL-6 expressing cells was also maintained. As a control, K6H6/B5 cells were infected with the empty vector (pMSCV puro). Expression of mIL-6 was confirmed with the Optikine mIL-6 ELISA kit (BD Biosciences).

Similar to the extopic expression of mIL-6, ectopic expression of hTERT was achieved using the retroviral expression plasmid, pMSCV hygro hTERT. Briefly, K6H6/B5 cells ectopically expressing mIL-6 were modified to express hTERT using a protocol described in Dessain et al., 2004, J Imm Methods 291: 109-122. Briefly, A retroviral transfer vector containing an hTERT cDNA in combination with a hygromycin selectable marker gene (MSCV hygro hTERT) was constructed using standard recombinant DNA techniques. Expression of hTERT was verified by RT-PCR.

The retroviral expression system used to express mIL-6 and hTERT allows for the random integration of the gene encoding mIL-6 and hTERT into the genome of the parental cell line. The integration site is not sequence specific, but rather is believed to be associated with chromatin structure (Michell et al., 2004 PLoS Biology 2: 1127-1137). Retroviral insertion biases have been estimated by a variety of methods reviewed in Uren et al., 2005 Oncogene 24: 7656-7672. There is evidence that there is a preference for integration close to DNAseI sensitive and/or hypomethylated regions suggesting that retroviral integration has a tendency to insert within actively transcribed regions of the genome. Other evidence suggests that retroviral integration preferentially occurs near gene promoters. Generally, the evidence suggests that retroviral integration is correlated with the target DNA's local characteristics, including conformation and methylation status, gene density, chromatin conformation, host DNA associated proteins and local transcriptional activity. Accordingly, retroviral integration is partially affected by nucelosome structure rather than any particular sequence specificity. Thus, the integration site is unpredictable.

Example 2

B5-6T Fusion Partner

An advantage of the B5-6T fusion partner cell line over other fusion partner cell lines is that the B5-6T cell line allows for the generation of hybridomas at an increased frequency. Without wishing to be bound by any theory, it is believed that this is attributed to the stable ectopic expression of hTERT compared to the expression of hTERT from prior fusion partners, such as the SP2/mL-6 MP hTERT (MPT) cell line (a murine cell line that ectopically expresses murine mIL-6 and hTERT).

Compared to the SP2/mL-6 MPT cell line, the B5-6T cell line was observed to maintain stable ectopic expression of hTERT after a period of culturing in vitro. FIG. 1A shows that 6 out of 6 sub-clones generated from an SP2/mL-6 MPT cell line lost ectopic expression of hTERT over time (FIG. 1A). However, sub-clones generated from the B5-6T cell line cell maintained hTERT expression following cloning (FIG. 1B).

A comparative study of the fusion efficiency of several fusion partner was assessed. Peripheral blood lymphocytes were fused with the following fusion partner cell lines: MPT, K6H6/B5, and B5-6T. 10 wells from each fusion were plated and selected in HAT medium (Sigma-Aldrich). The fusion efficiency was determined by counting the number of clones in each well. It was observed that in all 10 wells, the B5-6T fusion partner cell line resulted in a larger number of hybridomas compared to the other fusion partner cell lines (FIG. 2).

These results demonstrate that the B5-6T fusion partner cell line efficiently forms stable human antibody-secreting hybridomas through cell fusion with primary human B-lymphocytes at an increased frequency. The hybridomas are able to maintain secretion of human antibodies derived from the primary B-lymphocytes through multiple rounds of passaging.

Example 3

Generation of the 13A Hybridoma

The 13A hybridoma was generated as follows. Heparinized peripheral blood was obtained following informed consent from volunteers vaccinated with the pentavalent botulinum toxoid vaccine. All BoNT-immune blood samples were obtained on the 8$^{th}$ day following the last dose of the pentavalent botulinum toxoid vaccine. The peripheral blood mononuclear cell (PBMC) fraction was isolated using gradient density centrifugation with FicollPaque PLUS (GE Healthcare, Piscataway, N.J.). Purified PBMCs were used fresh or after frozen storage in 90% heat-inactivated fetal calf serum (FCS, Invitrogen, Carlsbad, Calif.) 10% DMSO (Sigma-Aldrich, St. Louis, Mo.).

Prior to cell fusion with the B5-6T fusion partner cell line, the primary peripheral blood lymphocytes were cultured in Advanced RPMI/1% FCS/pen/strep (Invitrogen) with pokeweed mitogen (5 µg/ml), and optionally with BoNT/A (5 µg/ml, Hall strain, Metabiologics, Madison, Wis.) or recombinant BoNT/A kDa C-terminal domain peptide (5 µg/ml) for about 5 days.

The pokeweed mitogen stimulated cells were fused to fusion partner cells at a 1:1 ratio using the stirring method with 50% polyethylene glycol (Sigma-Aldrich) and selection in HAT medium (Sigma-Aldrich). Fused cells were seeded in 48-well plates at a density of $2\times10^5$ B-cells per well in the presence of a feeder layer of $1\times10^5$ C57BL/6 thymocytes/well. Hybrid cells were cloned at 1 cell/well in 96-well plates with $1\times10^5$ C57BL/6 thymocytes/well. After 3-4 rounds of cloning, stable IgG-secreting hybridomas were adapted to IS MAB-CD (Irvine Scientific, Santa Ana, Calif.), plated at a density of $5\times10^5$ cells/ml in 100 ml culture and incubated for 5 days in a 500 ml roller bottle. Filtered supernatants were purified over Protein G Sepharose columns (GE Healthcare). Purity was assessed using SDS-PAGE (Invitrogen). Protein concentrations were determined using the NanoDrop spectrophotometer (NanoDrop Technologies, Wilmington, Del.).

Hybrid cell pools were tested for human antibodies secreted into their supernatants that specifically bound BoNT/A by ELISA. Cells in a positive pool were cloned by limiting dilution. The specificity of the antibody for BoNT/A was verified by a limiting dilution ELISA.

BoNT/A antibodies were assayed using ELISAs as previously described using the recombinant 50 kD C-terminal BoNT/A domain (Kiyatkin et al., 1997 Infect Immun 65: 4586-4591), hereinafter "HC50A". EasyWash 96-well plates (Corning) were coated at 4° C. overnight with 100 µl/well HC50A (at 5 µg/ml) in PBS. Plates were washed with PBS/ 0.05% Tween-20 (Sigma-Aldrich) and then blocked for 1 hour at 37° C. with PBS/0.05% Tween-20/5% bovine calf serum/3% goat serum (Sigma-Aldrich). Hybridoma supernatants were added at 100 µl/well and incubated for 2 hours at 37° C., followed by a murine anti-human IgG HRP secondary antibody (9040-05, Southern Biotechnology, Birmingham, Ala.). OPD was used as the colorimetric substrate; optical density at 490 nm was measured. Identity of the light chain was confirmed with the HRP-conjugated specific goat polyclonal antibody A5175 (anti-lambda) (Sigma-Aldrich).

The 13A hybridoma was deposited under the terms of the Budapest Treaty with the American Type Culture Collection, 10801 University Blvd, Manassas, Va. 20110-2209, USA, on Jan. 15, 2008 and assigned ATCC Accession No. PTA-8871.

Example 4

Binding Measurements of 13A Antibody

The next set of experiments was designed to test the binding characteristic of the 13A antibody to botulinum neurotoxin. Solution phase affinity and association rate constants for the 13A antibody were determined using the Kinetic Exclusion Assay (KinExA) flow fluorimeter (Sapidyne Instruments, Boise, Id.). All experiments were performed at room temperature using tris buffer saline (10TBS-10 mM tris, 100 mM NaCl, 0.02% NaN$_3$, pH 8) as the running buffer. 10TBS augmented with 1 mM PMSF and 1 mg/ml BSA was used as the sample buffer. HC50A was covalently coupled to polymethyl methacrylate beads (PMMA, ~98 µm average size, Sapidyne Instruments) and used as the assay capture reagent. Captured antibody was detected with a goat anti-human Rhodamine labeled secondary antibody (0.5 (g/ml) (Jackson ImmunoResearch, West Grove, Pa.).

HC50A was purified by passage over a Superdex 5200 size exclusion column (GE Healthcare). HC50A concentration was assessed using the Edelhoch method and an absorptivity coefficient of 87050 as published in Edelhoch, 1967 Biochemistry 6: 1948-1954. Equilibrium experiments were prepared by serially diluting HC50A into solutions with a constant concentration of antibody (either 1 nM or 100 pM). Equilibration times were determined empirically by running sample sets multiple times until a stable calculated KD was reached. Equilibrium data were fit to a 1:1 binding model using manufacturer's software that included a drift correction factor (Version 2.4; Sapidyne Instruments).

Association rate experiments were performed using the "Direct Kinetics" method, where a binding of mAb and HC50A in a single reaction was followed as a function of time as the reaction progressed to equilibrium (Luginbuhl et al., 2006 J Mol Biol 363: 75-97). Kinetic experiments were fit to a general bimolecular association model included in the software. Dissociation rate constants were calculated as the product of $KD \times k_{on}$.

A Biacore 3000 (GE Healthcare) biosensor was used for the surface plasmon resonance (SPR) kinetic measurements. 13A antibody was immobilized using standard EDC/NHS chemistry to a CM5 sensor chip achieving approximately 240 RU signal prior to blocking. HC50A was diluted into HEPES buffered saline containing 0.005% surfactant P-20 (HBS-P) at concentrations ranging from 400-50 pM. 240 µL of each HC50A dilution was injected (60 µl/min) over the immobilized antibody. Antigen was allowed to dissociate for 30 minutes prior to two 45 µl injections of glycine, pH 2.0 to regenerate the surface. Data was globally fit using the 1:1 binding model with mass transport term included in the BIAevaluation software (Version 4.1, GE Healthcare). The KD was calculated as the quotient of $k_{off}$ and $k_{on}$.

Figure 3A:
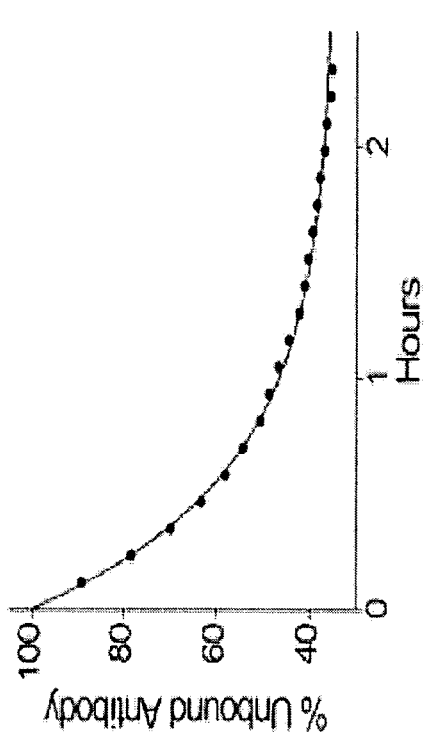
FIGS. 3A and 3B is a chart demonstrating the binding characteristic of the botulinum neurotoxin 13A antibody to the C-terminal 50 kd) domain of type A (HC50A).
Figure 3B:
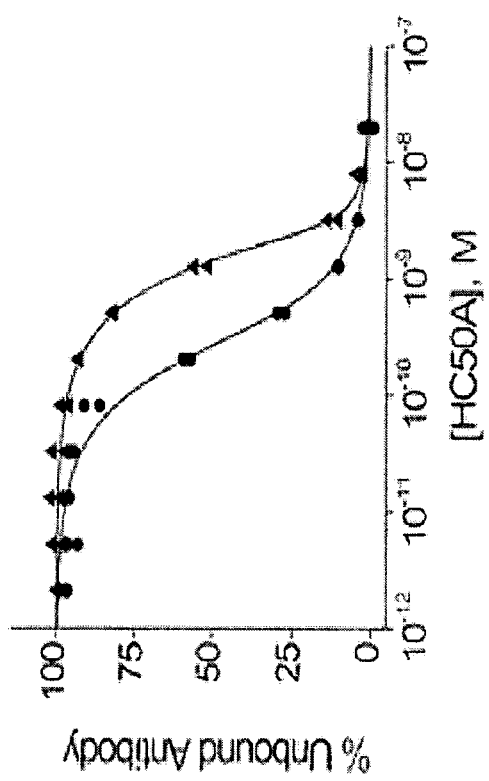

The results demonstrate that the 13A antibody specifically bound to HC50A, but did not bind the corresponding domains of BoNT serotypes B and E (HC50B and HC50E). A calculated KD of $5.2 \times 10^{-11}$ M was determined using the Biacore, which was similar to the determined KD value of $9.7 \times 10^{-11}$ M using the KinExA (FIG. 3B). A notable feature of the 13A binding kinetics is its fast on-rate, estimated to be $1.7 \times 10^7$ $M^{-1}s^{-1}$ by Biacore and $7.2 \times 10^6$ $M^{-1}s^{-1}$ by KinExA (FIG. 3A), which is a value that is about 8-fold or greater than those measured for comparable murine hybridoma or phage display antibodies.

Example 5

Botulinum Toxin Neutralization Activity of the Antibodies

Mouse protection assays were performed with 25 gram Swiss-Webster mice. The specified amount of BoNT/A was mixed for 1 hour at room temperature with concentrated hybridoma supernatant prior to tail-vein injection. For example, 10 pg BoNT/A (~2.5 LD50) was incubated with 100 µg antibody or control cell culture medium for 1 hour at room temperature prior to intravenous administration. For testing the antibody in mice, cell supernatants were concentrated 10-20 fold using an Amicon concentrator (Millipore, Billerica, Mass.) prior to testing in mice. The concentrated protein was quantitated using a NanoDrop spectrophotometer (NanoDrop Technologies, Wilmington, Del.).

It was observed that the 13A antibody neutralized BoNT/A in vivo, thus partially protecting a mouse from a lethal dose of toxin. In this experiment, 6 Swiss-Webster mice that received 10 pg BoNT/A with a control cell culture medium were dead within 18 hrs. It was observed that mice (n=6) that received the 10 pg BoNT/A mixed with 100 microliters of concentrated hybridoma supernatant containing 100 micrograms of the 13A antibody survived until the second day following the injection (~48 hours).

Example 6

Cloning of Antibodies cDNAs of the heavy chain and light chain variable domains of the 13A antibody was cloned from the hybridoma ATCC PTA-8871 using standard RT-PCR techniques. Primers for the heavy chain N-terminal regions, including the variable domain, were taken from Campbell et al. (1992, Mol. Immunol. 29:193-203). Primers for the kappa light chain regions were taken from Marks et al. (1991, Eur J. Immunol. 21:985-91). Primers for the lambda light chain were taken from Coronella et al. (2000 Nucleic Acids Res. 28:E85). Following RT-PCR, the amplified DNA fragments were cloned into the plasmid pCRTOPO 2.1 (Invitrogen, Carlsbad, Calif.) and sequenced. Fragments were sequenced by the Kimmel Cancer Center Nucleic Acid Sequencing Core facility at the Thomas Jefferson University, and DNA sequences were analyzed using the V-Quest program (Lefranc et al., 2005 Nucleic Acids Res 33: D593-597.

The following are the sequences:

13A Heavy chain DNA sequence,
SEQ ID NO: 1
gaggtgcagctggtggagtctggggagggttagtacagccagggcggtc cctgagactctcctgtacagcctctggattcacctttggtgattctgcca tgagctgggtccgccaggctccagggaaggggctggagtgggtaggtttc attagaggtaaaccttatggagggaaaccagaatacgccgcgtctgtgaa aggcagattcaccatttcaagagacgattccaagagcatcgcctatctgc aaatgaacagcctgaaaaccgaggacacagccgtgtattactgtactgca gggatgactacggtgactatttatgactactggggcagggaaccctggt caccgtctcctcagcaagcaccaag;

13A Heavy chain DNA sequence variable domain
(CDR1-CDR3),
SEQ ID NO: 2
ggattcacctttggtgattctgccatgagctgggtccgccaggctccagg gaaggggctggagtgggtaggtttcattagaggtaaaccttatggaggga aaccagaatacgccgcgtctgtgaaaggcagattcaccatttcaagagac gattccaagagcatcgcctatctgcaaatgaacagcctgaaaaccgagga cacagccgtgtattactgtactgcagggatgactacggtgactatttatg actactgg;

13A Heavy chain amino acid sequence,
SEQ ID NO: 3
EVQLVESGGGLVQPGRSLRLSCTASGFTFGDSAMSWVRQAPGKGLEWVGF

IRKPYGGKPEYAASVKGRFTISRDDSKSIAYLQMNSLKTEDTAVYYCTAG

MTTVTIYDYWGQGTLVTVSSASTK;

13A Heavy chain amino acid sequence variable domain (CDR1-CDR3),

SEQ ID NO: 4

GFTFGDSAMSWVRQAPGKGLEWVGFIRKPYGGKPEYAASVKGRFTISRDD

SKSIAYLQMNSLKTEDTAVYYCTAGMTTVTIYDYW;

13A Light chain DNA sequence total sequenced domain,

SEQ ID NO: 5 cagccactctcagtgtcagtggccctgggacagacggccggaattacctg tgagggaaacaacattggaagtaaaaatgtgcattggtaccagcagaagc caggccaggcccctgtgctggtcatctatagggatagcaatcggccctct gggatccctgagcgattctctggcttcaactcggggaatacggccaccct gaccatcagcagagtccaagccggggatgaggctgactattactgtcagg tgtgggacagcagcactggggtgttcggcggagggaccgagctgaccgtc ctaggtcagcccaaggctgcccctcggtcactctgttcccgccctcctc tgaggagcttcaagccaacaaggccacactggtgtgtctcataagtgact tctacccgggagccgtgacagtggcctggaaggcagatagcagcccgtc aaggcgggagtggagaccaccacacctccaaacaaagcaacaacaagta cgcggccagcagctatctgagcctgacgcctgagcagtggaagtcccaca gaagctacagctgccagg;

13A Light chain DNA sequence variable domain (CDR1-CDR3),

SEQ ID NO: 6 aacattggaagtaaaaatgtgcattggtaccagcagaagccaggccaggc ccctgtgctggtcatctatagggatagcaatcggccctctgggatccctg agcgattctctggcttcaactcggggaatacggccaccctgaccatcagc agagtccaagccggggatgaggctgactattactgtcaggtgtgggacag cagcactggggtgttc;

13A Light chain amino acid sequence,

SEQ ID NO: 7

QPLSVSVALGQTAGITCEGNNIGSKNVHWYQQKPGQAPVLVIYRDSNRPS

GIPERFSGFNSGNTATLTISRVQAGDEADYYCQVWDSSTGVFGGGTELTV

LGQPKAAPSVTLFPPSSEELQANKATLVCLISDFYPGAVTVAWKADSSPV

KAGVETTTPSKQSNNKYAASSYLSLTPEQWKSHRSYSCQ;

13A Light chain amino acid sequence variable domain (CDR1-CDR3),

SEQ ID NO: 8

NIGSKNVHWYQQKPGQAPVLVIYRDSNRPSGIPERFSGFNSGNTATLTIS

RVQAGDEADYYCQVWDSSTGVF

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. The fusion partner cell line deposited as ATCC accession number PTA-8869.

2. A method of making a hybridoma, said method comprising fusing B-lymphocytes to cells of the fusion partner cell line of claim 1, thereby producing a hybridoma.

3. The method of claim 2, wherein said B-lymphocytes are cultured in vitro for a period of time in the presence of pokeweed mitogen prior to fusion with cells of the fusion partner cell line.

4. The method of claim 2, wherein said B-lymphocytes are isolated from a subject vaccinated with a botulinum vaccine.

5. A method of producing a monoclonal antibody, the method comprising fusing B-lymphocytes with cells of the fusion partner cell line of claim 1 to produce hybridomas; selecting a hybridoma that produces said monoclonal antibody; and culturing said hybridoma to produce said monoclonal antibody.

6. The method of claim 5, wherein said B-lymphocytes are cultured in vitro for a period of time in the presence of pokeweed mitogen prior to fusion with cells of the fusion partner cell line.

7. The method of claim 5, wherein said B-lymphocytes are isolated from a subject vaccinated with a botulinum vaccine.

* * * * *

SEQUENCE LISTING

<160> NUMBER OF SEQ ID NOS: 8

<210> SEQ ID NO 1
<211> LENGTH: 375
<212> TYPE: DNA
<213> ORGANISM: Homo sapiens

<400> SEQUENCE: 1

```
gaggtgcagc tggtggagtc tgggggaggg ttagtacagc cagggcggtc cctgagactc      60
tcctgtacag cctctggatt caccttggt gattctgcca tgagctgggt ccgccaggct     120
ccagggaagg gctggagtg gtaggtttc attagaggta aaccttatgg agggaaacca     180
gaatacgccg cgtctgtgaa aggcagattc accatttcaa gagacgattc caagagcatc     240
gcctatctgc aaatgaacag cctgaaaacc gaggacacag ccgtgtatta ctgtactgca     300
```

```
gggatgacta cggtgactat ttatgactac tggggccagg gaaccctggt caccgtctcc    360
tcagcaagca ccaag                                                    375

<210> SEQ ID NO 2
<211> LENGTH: 258
<212> TYPE: DNA
<213> ORGANISM: Homo sapiens

<400> SEQUENCE: 2
ggattcacct ttggtgattc tgccatgagc tgggtccgcc aggctccagg gaagggctg      60 gagtgggtag gtttcattag aggtaaacct tatggaggga aaccagaata cgccgcgtct   120
gtgaaaggca gattcaccat ttcaagagac gattccaaga gcatcgccta tctgcaaatg   180
aacagcctga aaccgagga cacagccgtg tattactgta ctgcagggat gactacggtg    240
actatttatg actactgg                                                 258

<210> SEQ ID NO 3
<211> LENGTH: 124
<212> TYPE: PRT
<213> ORGANISM: Homo sapiens

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Ser
            20                  25                  30

Ala Met Ser Trp Val Arg Gln Ala Pro Gly Lys Gly Leu Glu Trp Val
        35                  40                  45

Gly Phe Ile Arg Lys Pro Tyr Gly Gly Lys Pro Glu Tyr Ala Ala Ser
    50                  55                  60

Val Lys Gly Arg Phe Thr Ile Ser Arg Asp Asp Ser Lys Ser Ile Ala
65                  70                  75                  80

Tyr Leu Gln Met Asn Ser Leu Lys Thr Glu Asp Thr Ala Val Tyr Tyr
                85                  90                  95

Cys Thr Ala Gly Met Thr Thr Val Thr Ile Tyr Asp Tyr Trp Gly Gln
            100                 105                 110

Gly Thr Leu Val Thr Val Ser Ser Ala Ser Thr Lys
        115                 120

<210> SEQ ID NO 4
<211> LENGTH: 85
<212> TYPE: PRT
<213> ORGANISM: Homo sapiens

<400> SEQUENCE: 4

Gly Phe Thr Phe Gly Asp Ser Ala Met Ser Trp Val Arg Gln Ala Pro
1               5                   10                  15

Gly Lys Gly Leu Glu Trp Val Gly Phe Ile Arg Lys Pro Tyr Gly Gly
            20                  25                  30

Lys Pro Glu Tyr Ala Ala Ser Val Lys Gly Arg Phe Thr Ile Ser Arg
        35                  40                  45

Asp Asp Ser Lys Ser Ile Ala Tyr Leu Gln Met Asn Ser Leu Lys Thr
    50                  55                  60

Glu Asp Thr Ala Val Tyr Tyr Cys Thr Ala Gly Met Thr Thr Val Thr
65                  70                  75                  80

Ile Tyr Asp Tyr Trp
                85
```

<210> SEQ ID NO 5
<211> LENGTH: 568
<212> TYPE: DNA
<213> ORGANISM: Homo sapiens

<400> SEQUENCE: 5

```
cagccactct cagtgtcagt ggccctggga cagacggccg gaattacctg tgagggaaac      60
aacattggaa gtaaaaatgt gcattggtac cagcagaagc caggccaggc ccctgtgctg     120
gtcatctata gggatagcaa tcggccctct gggatccctg agcgattctc tggcttcaac     180
tcggggaata cggccaccct gaccatcagc agagtccaag ccggggatga ggctgactat     240
tactgtcagg tgtgggacag cagcactggg gtgttcggcg agggaccga gctgaccgtc     300
ctaggtcagc ccaaggctgc ccctcggtc actctgttcc cgccctcctc tgaggagctt     360
caagccaaca ggccacact ggtgtgtctc ataagtgact tctacccggg agccgtgaca     420
gtggcctgga aggcagatag cagccccgtc aaggcgggag tggagaccac cacaccctcc     480
aaacaaagca caacaagta cgcggccagc agctatctga gcctgacgcc tgagcagtgg     540
aagtcccaca gaagctacag ctgccagg                                        568
```

<210> SEQ ID NO 6
<211> LENGTH: 216
<212> TYPE: DNA
<213> ORGANISM: Homo sapiens

<400> SEQUENCE: 6

```
aacattggaa gtaaaaatgt gcattggtac cagcagaagc caggccaggc ccctgtgctg      60
gtcatctata gggatagcaa tcggccctct gggatccctg agcgattctc tggcttcaac     120
tcggggaata cggccaccct gaccatcagc agagtccaag ccggggatga ggctgactat     180
tactgtcagg tgtgggacag cagcactggg gtgttc                                216
```

<210> SEQ ID NO 7
<211> LENGTH: 189
<212> TYPE: PRT
<213> ORGANISM: Homo sapiens

<400> SEQUENCE: 7

```
Gln Pro Leu Ser Val Ser Val Ala Leu Gly Gln Thr Ala Gly Ile Thr
1               5                   10                  15

Cys Glu Gly Asn Asn Ile Gly Ser Lys Asn Val His Trp Tyr Gln Gln
            20                  25                  30

Lys Pro Gly Gln Ala Pro Val Leu Val Ile Tyr Arg Asp Ser Asn Arg
        35                  40                  45

Pro Ser Gly Ile Pro Glu Arg Phe Ser Gly Phe Asn Ser Gly Asn Thr
    50                  55                  60

Ala Thr Leu Thr Ile Ser Arg Val Gln Ala Gly Asp Glu Ala Asp Tyr
65                  70                  75                  80

Tyr Cys Gln Val Trp Asp Ser Ser Thr Gly Val Phe Gly Gly Gly Thr
                85                  90                  95

Glu Leu Thr Val Leu Gly Gln Pro Lys Ala Ala Pro Ser Val Thr Leu
            100                 105                 110

Phe Pro Pro Ser Ser Glu Glu Leu Gln Ala Asn Lys Ala Thr Leu Val
        115                 120                 125

Cys Leu Ile Ser Asp Phe Tyr Pro Gly Ala Val Thr Val Ala Trp Lys
    130                 135                 140
```

```
Ala Asp Ser Ser Pro Val Lys Ala Gly Val Glu Thr Thr Thr Pro Ser
145                 150                 155                 160

Lys Gln Ser Asn Asn Lys Tyr Ala Ala Ser Ser Tyr Leu Ser Leu Thr
                165                 170                 175

Pro Glu Gln Trp Lys Ser His Arg Ser Tyr Ser Cys Gln
            180                 185

<210> SEQ ID NO 8
<211> LENGTH: 72
<212> TYPE: PRT
<213> ORGANISM: Homo sapiens

<400> SEQUENCE: 8

Asn Ile Gly Ser Lys Asn Val His Trp Tyr Gln Gln Lys Pro Gly Gln
1               5                   10                  15

Ala Pro Val Leu Val Ile Tyr Arg Asp Ser Asn Arg Pro Ser Gly Ile
            20                  25                  30

Pro Glu Arg Phe Ser Gly Phe Asn Ser Gly Asn Thr Ala Thr Leu Thr
        35                  40                  45

Ile Ser Arg Val Gln Ala Gly Asp Glu Ala Asp Tyr Tyr Cys Gln Val
    50                  55                  60

Trp Asp Ser Ser Thr Gly Val Phe
65                  70
```